United States Patent
Ma et al.

(10) Patent No.: US 9,339,595 B2
(45) Date of Patent: *May 17, 2016

(54) DISPOSABLE VACUUM SOURCE AND MEDICAL APPLICATIONS THEREOF

(71) Applicants: Li Ma, Beijing (CN); Yongwang Li, Beijing (CN); Feng Ma, Cary, NC (US)

(72) Inventors: Li Ma, Beijing (CN); Yongwang Li, Beijing (CN); Feng Ma, Cary, NC (US)

(*) Notice: Subject to any disclaimer, the term of this patent is extended or adjusted under 35 U.S.C. 154(b) by 71 days.

This patent is subject to a terminal disclaimer.

(21) Appl. No.: 13/958,557

(22) Filed: Aug. 3, 2013

(65) Prior Publication Data

US 2013/0317389 A1  Nov. 28, 2013

Related U.S. Application Data

(63) Continuation of application No. 10/906,199, filed on Feb. 8, 2005, now Pat. No. 8,512,301.

(51) Int. Cl.
| | |
|---|---|
| *A61M 27/00* | (2006.01) |
| *A61M 1/00* | (2006.01) |
| *A61H 9/00* | (2006.01) |
| *A61B 5/15* | (2006.01) |
| *A61B 10/02* | (2006.01) |
| *A61B 17/44* | (2006.01) |
| *A61H 7/00* | (2006.01) |
| *A61H 39/04* | (2006.01) |
| *A61M 19/00* | (2006.01) |

(52) U.S. Cl.
CPC ........ *A61M 1/0023* (2013.01); *A61B 5/150099* (2013.01); *A61B 10/0291* (2013.01); *A61B 17/442* (2013.01); *A61H 7/00* (2013.01); *A61H 9/005* (2013.01); *A61H 39/04* (2013.01); *A61M 1/008* (2013.01); *A61M 1/0011* (2013.01); *A61M 19/00* (2013.01)

(58) Field of Classification Search
CPC ....... A61M 1/00; A61M 27/00; A61M 39/00; A61M 39/04; A61M 39/22; A61M 39/24; A61M 39/26; A61M 39/28; F04B 1/00; F04B 1/06; F04B 1/063; F04B 9/00; F04B 35/00; F04B 35/01; F04B 35/04; F04B 35/06; F04B 43/04; F04B 43/107; F04B 45/00
See application file for complete search history.

(56) References Cited

U.S. PATENT DOCUMENTS

| | | | | |
|---|---|---|---|---|
| 5,141,503 A | * | 8/1992 | Sewell, Jr. | 604/317 |
| 2002/0087131 A1 | * | 7/2002 | Wolff et al. | 604/319 |

* cited by examiner

*Primary Examiner* — Melanie Hand
(74) *Attorney, Agent, or Firm* — Syncoda LLC; Feng Ma

(57) ABSTRACT

An apparatus including: a vacuum container configured to provide and substantially maintain a built-in vacuum pressure; a contact member configured to contact and substantially enclose a surface area; a vacuum device configured to couple the built-in vacuum pressure to the surface area thereby applying a suction force over the surface area; and a conduit coupled to the vacuum container; wherein the vacuum container is also configured to retain a substance collected from adjacent the surface area, wherein the conduit is configured to direct the substance to the vacuum container, and to maintain substantially the same level of vacuum pressure as the vacuum container, wherein the vacuum container comprises a collapsible container, and wherein the collapsible container comprises a spring member configured to maintain a tension in a wall of the vacuum container.

20 Claims, 2 Drawing Sheets

DISPOSABLE VACUUM SOURCE AND MEDICAL APPLICATIONS THEREOF

CROSS-REFERENCE TO RELATED APPLICATIONS

The present application is a continuation-in-part of U.S. patent application Ser. No. 10/906,199 (now Pat. No. 8,512, 301), filed on Feb. 8, 2005, the disclosure of which is hereby incorporated by reference in its entirety.

BACKGROUND

Conventional vacuum sources, such as those powered by electrical pumps, find applications in a variety of areas, such as household cleaning, pumping, etc.

SUMMARY

In an aspect, an apparatus is provided including: a vacuum container configured to provide and substantially maintain a built-in vacuum pressure; a contact member configured to contact and substantially enclose a surface area; a vacuum device configured to couple the built-in vacuum pressure to the surface area thereby applying a suction force over the surface area; and a conduit coupled to the vacuum container; wherein the vacuum container is also configured to retain a substance collected from adjacent the surface area, wherein the conduit is configured to direct the substance to the vacuum container, and to maintain substantially the same level of vacuum pressure as the vacuum container, wherein the vacuum container comprises a collapsible container, and wherein the collapsible container comprises a spring member configured to maintain a tension in a wall of the vacuum container.

In some embodiments, the vacuum device includes: a first valve configured to, if opened, couple the built-in vacuum pressure to the surface area; and a second valve configured to equalize a pressure over the surface area with an ambient atmospheric pressure thereby releasing the suction force.

In some embodiments, the first valve, if closed, is also configured to maintain a pressure difference between the vacuum container and the surface area.

In some embodiments, the vacuum device includes a first vacuum valve configured to equalize the built-in vacuum pressure with the pressure on the surface area.

In some embodiments, the vacuum device further includes a second vacuum valve configured to release the suction force from the surface area.

In some embodiments, the vacuum apparatus further includes a needle and a catheter, wherein the suction force is configured for fixation of the needle and the catheter, and wherein the apparatus is configured as an anesthesia apparatus.

In some embodiments, the vacuum apparatus further includes a needle, wherein the apparatus is configured as a disposable lancing apparatus.

In some embodiments, the vacuum apparatus further includes a suction tube, and wherein the apparatus is configured as a uterine tissue extraction device.

In some embodiments, the vacuum device includes a suction cup, and wherein the apparatus is configured as a fetal attraction apparatus.

In another aspect, a vacuum apparatus is provided including: a vacuum container configured to provide and substantially maintain a built-in vacuum pressure; a contact member configured to contact and substantially enclose a surface area; a vacuum device configured to couple the built-in vacuum pressure to the surface area thereby applying a suction force over the surface area; wherein the vacuum container is also configured to retain a substance collected from adjacent the surface area, wherein the vacuum container comprises a collapsible container, and wherein the collapsible container comprises a spring member configured to maintain a tension in a wall of the vacuum container; wherein the vacuum device comprises: a first valve configured to apply the built-in vacuum pressure to the surface area thereby causing the contact member to apply a suction force over the surface area; and a second valve configured to couple an ambient atmospheric pressure to the surface area thereby releasing the surface area from the suction force.

In some embodiments, the contact member comprises a funnel.

In some embodiments, the vacuum apparatus is configured as an acupressure therapy apparatus.

In some embodiments, the vacuum apparatus is configured as a skin care apparatus.

In some embodiments, the vacuum apparatus is configured as a physical therapy apparatus.

In another aspect, a method is provided including: providing and substantially maintaining a built-in vacuum pressure with a vacuum container; contacting and substantially enclosing a surface area with a contact member; coupling the built-in vacuum pressure to the surface area thereby applying a suction force over the surface area with a vacuum device; directing, with a conduit coupled to the vacuum container, the substance to the vacuum container, wherein the conduit is also configured to maintain substantially the same level of vacuum pressure as the vacuum container; wherein the vacuum container comprises a collapsible container and is configured to retain a substance collected from adjacent the surface area with the vacuum container; and wherein the collapsible container comprises a spring member configured to maintain a tension in a wall of the vacuum container.

In some embodiments, said contacting and substantially enclosing a surface area with a contact member comprises contacting and substantially enclosing an acupressure point on a patient's skin; the method further comprising releasing the suction force by equalizing the pressure on the skin with an ambient atmospheric pressure.

In some embodiments, said contacting and substantially enclosing a surface area with a contact member comprises contacting and substantially enclosing a skin area for skin care.

In some embodiments, said contacting and substantially enclosing a surface area with a contact member comprises contacting and substantially enclosing an area of a patient's skin for physical therapy.

In some embodiments, said contacting and substantially enclosing a surface area with a contact member comprises contacting and substantially enclosing an area of a patient's skin, the method further comprising fixing an anesthesia needle/catheter adjacent the area of the patient's skin.

In some embodiments, said contacting and substantially enclosing a surface area with a contact member comprises contacting and substantially enclosing a uterine tissue, the method further comprising extracting and retaining the uterine tissue with the vacuum container.

DETAILED DESCRIPTION

Just as carbonated drink bottles or cans that hold a "positive" pressure, an apparatus in accordance embodiments of the present invention maintains a "negative", or vacuum pressure. The term "vacuum" in the present application has its ordinary meaning, "capable of creating a differential pressure", "isolated", or "a state of being sealed off from external or environmental influences". The material or structure of the apparatus is designed to maintain such a negative pressure. It is foreseeable that the cost of such a vacuum container is comparable to a soda can or bottle.

Figure 1:
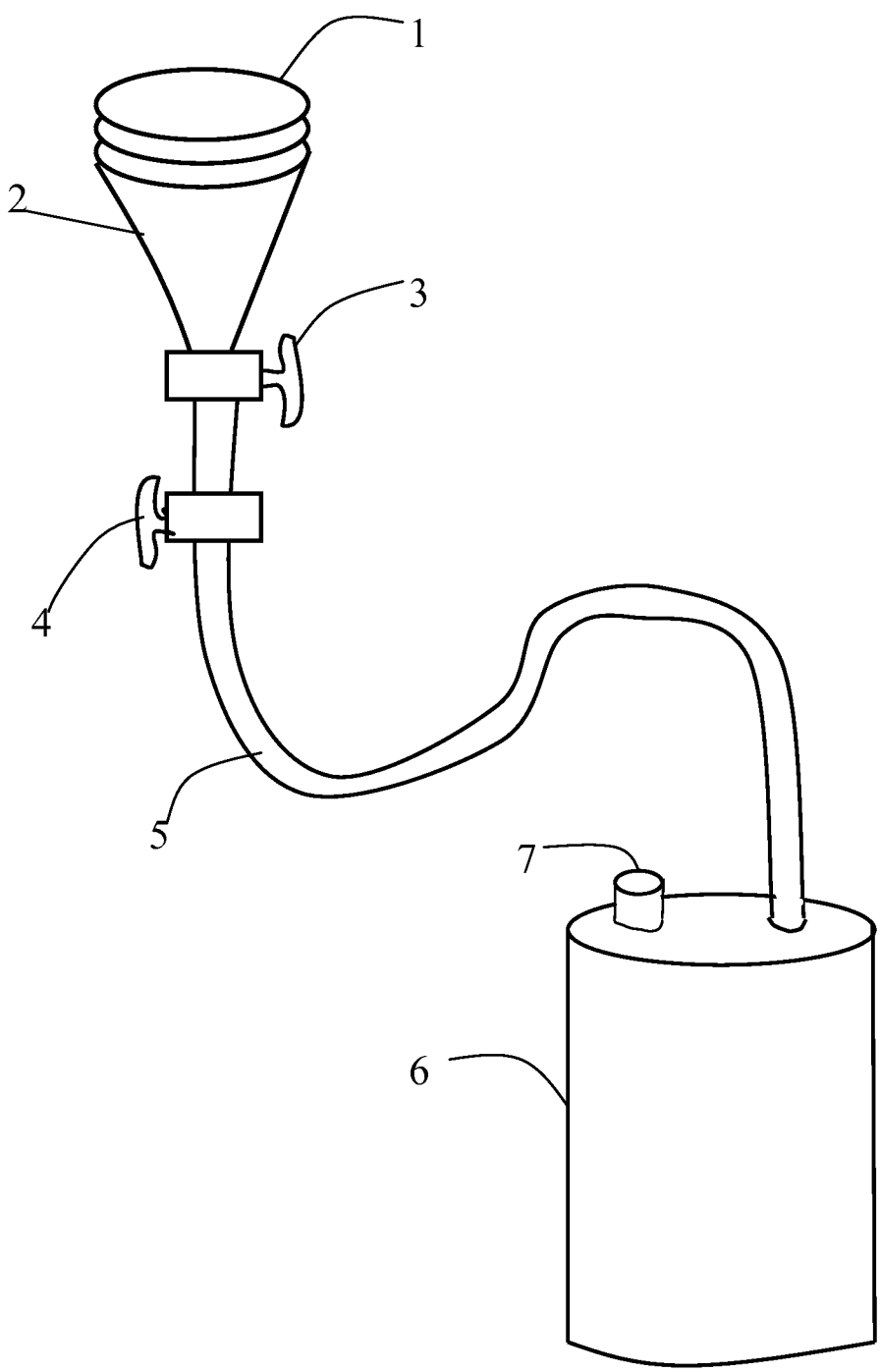
FIG. 1 illustrates a disposable vacuum apparatus according to some embodiments.

FIG. 1 illustrates a urine collection kit in accordance with embodiments of the present invention, wherein a ring-shaped vacuum seal 1 is used for a female urine orifice. A lower part of an extendable funnel 2 seals a male penis. A first valve 3 is used to connect the funnel 2 with the ambient atmosphere to release the vacuum pressure inside the funnel 2, thus releasing the suction force on the skins. A second valve 4 connects the funnel 2 with a tube 5 and a container 6. A removable cap 7 may be used to dump or collect the urine and pump out the air for a possible reuse of the kit.

When used as a urine collection kit, the apparatus as illustrated in FIG. 1 may have the funnel work as a receptacle connected to the container that maintains a built-in vacuum pressure. In the case of a solid container illustrated in FIG. 1, the vacuum pressure is supported by the tension of the container wall. In the case of a collapsible container, the built-in vacuum pressure may be supported by a reusable supporting structure. The built-in vacuum pressure serves as a means to collect urine, and to prevent spillage of the fluid, and to help contain the odor within the container. The apparatus provides a suction force for a comfortable yet airtight seal between the receptacle and a urinating organ of a male or female user. The apparatus is stored with the container maintaining a vacuum pressure. When in use, after fitting the receptacle with skins around the urine outlet, the second valve connecting the receptacle and the container is opened. Thus, the receptacle, the connecting tube, and the container are connected with the same built-in vacuum pressure, supported by the tension from the container wall or from the supporting structure. After usage, the second valve is closed to isolate the tube and the container, which still maintain a pressure lower than the ambient atmospheric pressure thus retaining the liquid as well as the odor. A first valve is then opened to connect the receptacle with the ambient atmosphere, thus releasing the receptacle from the vacuum pressure. The entire kit, except the optional re-usable supporting structure, can be disposed or recycled or utilized for extracting useful chemicals from the urine.

Figure 2:
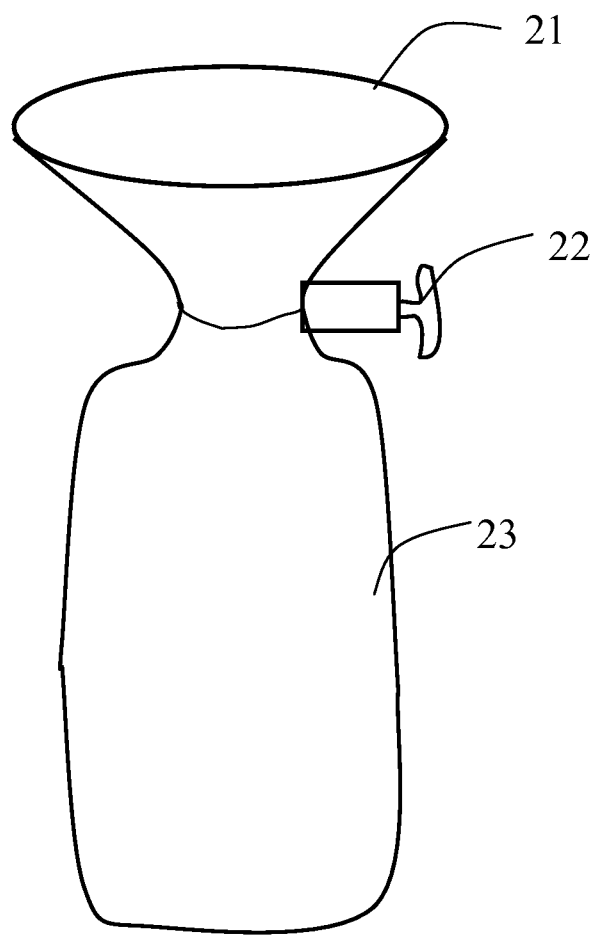
FIG. 2 illustrates an apparatus providing a suction force to be used in various medical applications according to some embodiments.

FIG. 2 illustrates an embodiment that may be used as a tool for physical therapy. A vacuum seal 21 may be used for skin contact. The size of the opening of the seal 21 is determined by the purpose of usage. A small opening applying suction force on a small area of skin may be used to treat skin acne. A large opening can be used for physical therapy. A valve 22 connects a vacuum container 23 with the vacuum seal 21. When the valve 22 is opened, the vacuum suction force is applied to the skin in contact with the seal 21. The ratio between the volume of the container 23 and the volume contained between the skin and the vacuum seal 21 determines the suction force applied.

In one preferred embodiment, the invention includes a collapsible container with a restoring tension provided by external spring-like structure that provides the suction force. The examples described in this section are for illustrative purpose only and should not be interpreted to be limiting. It should be obvious to one skilled in the art to recognize that other alternative embodiments are possible to implement the essential ideas of the present invention.

Three examples of alternate embodiments of the present invention include: (1) A solid plastic bottle with a built-in vacuum pressure. The bottle cannot be collapsed. This may provide the strongest vacuum pressure but needs more storage space. (2) A collapsed plastic bottle. The container structure is manufactured such that it has a built-in tension from skeleton-like structures to recover the shape of the container to a non-collapsed state, thus providing the suction force. (3) A collapsed container with a supporting structure. The supporting structure can be made with stainless steel or materials alike with a strong tension that supports the sucking force of the container. The supporting structure can be re-used as it does not have contact with the urine.

A vacuum pump may be provided to users who prefer to reuse the kit. The pump can be connected to the removable cap of the container, and pump the container to a certain vacuum level.

The pump can be an either electrical or manual pump, with the output vacuum pressure adjustable according to users' comfort level.

Other applications of the present invention include a universal disposable vacuum source that can be applied to other areas of applications. For example, in traditional Chinese medicine, a suction force is needed to apply to the acupressure points on the patients, to achieve effects similar to acupuncture. The suction force has been achieved by setting fire in a small container placed on the patient's skin corresponding to the acupressure points, followed by a procedure of applying a small pot to cover the fire. The fire burns out oxygen in the small pot and causes a suction force from the partial vacuum. In this procedure, there is an obvious hazard of fire and a difficulty in controlling the strength of the suction force. Using the canned vacuum source in accordance with embodiments of the present invention, one can easily apply plastic cans of various sizes and vacuum pressure of different strengths on the patient. The cans can be disposable to save the cost of disinfections.

Another method of using embodiments in accordance with the present invention is to manufacture small plastic tubes with built-in vacuum, which can be used in skin care industry to provide a clean, ease-to-use, and disposable source of suction force to treat acne and to extract secretions from skin follicles.

Another method of using embodiments in accordance with the present invention is to manufacture vacuum cans with various sizes that can be applied to patient skins after plastic surgery to help maintain the desired shape of the patient body, or to collect secretions after the surgery, or to use as a tool for physical therapy.

The disposable vacuum apparatus disclosed herein can also be used in a number of applications, particularly when power is not available to continuously generate vacuum, and/or when the cost and time do not justify cleaning and disinfection of devices in medical applications. Such applications are particularly important in disaster relief, battle field, emergencies, etc.

For example, the disposable vacuum source can be used in obstetrics and gynecology, such as applying an attraction force to uterine tissues. Negative pressure can be generated using the disposable vacuum source disclosed herein, through a suction tube. The suction tube can be slowly inserted into the uterine cavity of a patient. The vacuum device can properly regulate the pressure, and the suction tube moved inside the uterine to extract tissues, until the tissues are extracted. Similar disposable vacuum sources can also be used in endometrial infertility testing, and endometrial biopsy. In obstetrics, the vacuum device can be a suction cup, and the vacuum force from the disposable vacuum source can be used in a fetal attraction apparatus, and a Ventouse cup.

In some other examples, the disposable vacuum source can be used in anesthesiology, particularly in emergency medicine, and in mobile military surgical hospital applications. For example, the disposable vacuum source can be part of a disposable vacuum lancing apparatus for collecting blood samples and/or body fluid such as wound secretion, a suction device, an anesthesia needle/catheter fixation device, etc.

Advantages of the present invention include one or more of the following: (a) a low-cost one-time vacuum source that can have many applications; (b) when used as a disposable urine collection kit, the built-in vacuum pressure helps retain the urine and the odor; (c) the strength of the suction force can be designed and manufactured based on the vacuum pressure level, which in turn is determined by the material and structural design of the container.

While the invention has been described with respect to a limited number of embodiments, those of ordinary skill in the art, having benefit of this disclosure, will appreciate that other embodiments can be advised which do not depart from the scope of the invention as disclosed herein. For example, the "valve" in this disclosure will be recognized by one or ordinary skill in the art that it may be any types of valves to isolate and to connect the built-in vacuum with the ambient atmospheric pressure, and the container may be made of any types of materials or structures as long as it has sufficient strength to retain the built-in vacuum pressure. Accordingly, the scope of the invention should be limited only by the attached claims.

The invention claimed is:

1. An apparatus, comprising:
   a vacuum container configured to provide and substantially maintain a built-in vacuum pressure;
   a contact member configured to contact and substantially enclose a surface area;
   a vacuum device configured to couple the built-in vacuum pressure to the surface area thereby applying a suction force over the surface area; and
   a conduit coupled to the vacuum container;
   wherein the vacuum container is also configured to retain a substance collected from adjacent the surface area,
   wherein the conduit is configured to direct the substance to the vacuum container, and to maintain substantially the same level of vacuum pressure as the vacuum container,
   wherein the vacuum container comprises a collapsible container, and wherein the collapsible container comprises a spring member configured to maintain a tension in a wall of the vacuum container.

2. The apparatus of claim 1, wherein the vacuum device comprises:
   a first valve configured to, if opened, couple the built-in vacuum pressure to the surface area; and
   a second valve configured to equalize a pressure over the surface area with an ambient atmospheric pressure thereby releasing the suction force.

3. The apparatus of claim 2, wherein the first valve, if closed, is also configured to maintain a pressure difference between the vacuum container and the surface area.

4. The apparatus of claim 1, wherein the vacuum device comprises a first vacuum valve configured to equalize the built-in vacuum pressure with the pressure on the surface area.

5. The apparatus of claim 4, wherein the vacuum device further comprises a second vacuum valve configured to release the suction force from the surface area.

6. The apparatus of claim 1, further comprising a needle and a catheter, wherein the suction force is configured for fixation of the needle and the catheter, and wherein the apparatus is configured as an anesthesia apparatus.

7. The apparatus of claim 1, further comprising a needle, wherein the apparatus is configured as a disposable lancing apparatus.

8. The apparatus of claim 1, further comprising a suction tube, and wherein the apparatus is configured as a uterine tissue extraction device.

9. The apparatus of claim 1, wherein the vacuum device comprises a suction cup, and wherein the apparatus is configured as a fetal attraction apparatus.

10. A vacuum apparatus, comprising:
    a vacuum container configured to provide and substantially maintain a built-in vacuum pressure;
    a contact member configured to contact and substantially enclose a surface area;
    a vacuum device configured to couple the built-in vacuum pressure to the surface area thereby applying a suction force over the surface area;
    wherein the vacuum container is also configured to retain a substance collected from adjacent the surface area,
    wherein the vacuum container comprises a collapsible container, and
    wherein the collapsible container comprises a spring member configured to maintain a tension in a wall of the vacuum container;
    wherein the vacuum device comprises:
    a first valve configured to apply the built-in vacuum pressure to the surface area thereby causing the contact member to apply a suction force over the surface area; and
    a second valve configured to couple an ambient atmospheric pressure to the surface area thereby releasing the surface area from the suction force.

11. The vacuum apparatus of claim 10, wherein the contact member comprises a funnel.

12. The vacuum apparatus of claim 10, wherein the vacuum apparatus is configured as an acupressure therapy apparatus.

13. The vacuum apparatus of claim 10, wherein the vacuum apparatus is configured as a skin care apparatus.

14. The vacuum apparatus of claim 10, wherein the vacuum apparatus is configured as a physical therapy apparatus.

15. A method, comprising:
    providing and substantially maintaining a built-in vacuum pressure with a vacuum container;
    contacting and substantially enclosing a surface area with a contact member;
    coupling the built-in vacuum pressure to the surface area thereby applying a suction force over the surface area with a vacuum device;
    directing, with a conduit coupled to the vacuum container, the substance to the vacuum container, wherein the conduit is also configured to maintain substantially the same level of vacuum pressure as the vacuum container;
    wherein the vacuum container comprises a collapsible container and is configured to retain a substance collected from adjacent the surface area with the vacuum container; and wherein the collapsible container comprises a spring member configured to maintain a tension in a wall of the vacuum container.

16. The method of claim 15, wherein said contacting and substantially enclosing a surface area with a contact member comprises contacting and substantially enclosing an acupressure point on a patient's skin; the method further comprising releasing the suction force by equalizing the pressure on the skin with an ambient atmospheric pressure.

17. The method of claim 15, wherein said contacting and substantially enclosing a surface area with a contact member comprises contacting and substantially enclosing a skin area for skin care.

18. The method of claim 15, wherein said contacting and substantially enclosing a surface area with a contact member comprises contacting and substantially enclosing an area of a patient's skin for physical therapy.

19. The method of claim 15, wherein said contacting and substantially enclosing a surface area with a contact member comprises contacting and substantially enclosing an area of a patient's skin, the method further comprising fixing an anesthesia needle/catheter adjacent the area of the patient's skin.

20. The method of claim 15, wherein said contacting and substantially enclosing a surface area with a contact member comprises contacting and substantially enclosing a uterine tissue, the method further comprising extracting and retaining the uterine tissue with the vacuum container.

\* \* \* \* \*